(12) United States Patent
Wang et al.

(10) Patent No.: US 12,188,074 B2
(45) Date of Patent: Jan. 7, 2025

(54) METHODS FOR REDUCING CONDENSATION

(71) Applicant: Saudi Arabian Oil Company, Dhahran (SA)

(72) Inventors: Wei Wang, Quincy, MA (US); Hooisweng Ow, Woburn, MA (US); Sehoon Chang, Boston, MA (US)

(73) Assignee: Saudi Arabian Oil Company, Dhahran (SA)

( * ) Notice: Subject to any disclaimer, the term of this patent is extended or adjusted under 35 U.S.C. 154(b) by 995 days.

(21) Appl. No.: 17/030,914

(22) Filed: Sep. 24, 2020

(65) Prior Publication Data

US 2021/0095318 A1 Apr. 1, 2021

Related U.S. Application Data

(60) Provisional application No. 62/908,134, filed on Sep. 30, 2019.

(51) Int. Cl.
*C12P 7/16* (2006.01)
*B82Y 40/00* (2011.01)
(Continued)

(52) U.S. Cl.
CPC ............... *C12P 7/16* (2013.01); *C01B 33/12* (2013.01); *C01C 1/086* (2013.01); *C08G 61/124* (2013.01);
(Continued)

(58) Field of Classification Search
None
See application file for complete search history.

(56) References Cited

U.S. PATENT DOCUMENTS 7,585,817 B2   9/2009 Pope et al.
8,541,060 B2   9/2013 Messersmith et al.
(Continued)

FOREIGN PATENT DOCUMENTS

CN   106215892 A   * 12/2016   ............ B01J 20/268
CN   105907380 B     10/2017
(Continued)

OTHER PUBLICATIONS

International Search Report and Written Opinion dated Dec. 18, 2020 pertaining to International application No. PCT/US2020/051221 filed Sep. 17, 2020, 13 pgs.
(Continued)

*Primary Examiner* — Randy P Gulakowski
*Assistant Examiner* — Ha S Nguyen
(74) *Attorney, Agent, or Firm* — DINSMORE & SHOHL LLP

(57) ABSTRACT

A method for reducing condensate in a subsurface formation is disclosed. The method includes introducing a reactive mixture including an aqueous solution, urea, dopamine, a silica nanoparticle precursor, a silane grafting compound, and an alcohol compound into the subsurface formation. The method also includes allowing generation of ammonia through thermal decomposition of the urea and allowing the silica nanoparticle precursor to hydrolyze, thereby forming silica nanoparticles. The method further includes allowing the silane grafting compound to graft onto the silica nanoparticles, thereby forming functionalized silica nanoparticles. The method also includes allowing polymerization of the dopamine, thereby forming polydopamine. The method
(Continued)

also includes allowing the functionalized silica nanoparticles to attach to the subsurface formation via the polydopamine, thereby reducing condensate in the subsurface formation.

20 Claims, 1 Drawing Sheet

(51) Int. Cl.
  *C01B 33/12* (2006.01)
  *C01C 1/08* (2006.01)
  *C08G 61/12* (2006.01)
  *C09K 8/524* (2006.01)
  *C09K 8/84* (2006.01)
  *C09K 8/86* (2006.01)
  *E21B 43/241* (2006.01)

(52) U.S. Cl.
  CPC ............ *E21B 43/241* (2013.01); *B82Y 40/00* (2013.01); *C01P 2004/64* (2013.01)

(56) References Cited

U.S. PATENT DOCUMENTS

| | | | |
|---|---|---|---|
| 8,716,198 | B2 | 5/2014 | Iaconelli et al. |
| 8,911,831 | B2 | 12/2014 | Messersmith et al. |
| 9,353,309 | B2 | 5/2016 | Pope et al. |
| 9,694,388 | B2 | 7/2017 | Curran et al. |
| 9,783,725 | B1 | 10/2017 | Jiang et al. |
| 2009/0011222 | A1 | 1/2009 | Xiu et al. |
| 2011/0136704 | A1 | 6/2011 | Sharma et al. |
| 2015/0240608 | A1* | 8/2015 | Stehle ............... E21B 43/16 166/305.1 |
| 2017/0335163 | A1* | 11/2017 | Jiang ................. C09K 8/035 |
| 2018/0244985 | A1 | 8/2018 | Almohsin et al. |

FOREIGN PATENT DOCUMENTS

| | | |
|---|---|---|
| WO | 2014027825 A1 | 2/2014 |
| WO | 2014119913 A1 | 8/2014 |
| WO | 2018004560 A1 | 1/2018 |

OTHER PUBLICATIONS

Abhishek et al., "Wettability Alteration in Carbonate Reservoirs Using Nanofluids", Petroleum Science and Technology, vol. 33, pp. 794-801, 2015.

Al-Anssari et al., "Wettability alteration of oil-wet carbonate by silica nanofluid", Journal of Colloid and Interface Science, http://dx.doi.org/10.1016/j.jcis.2015.09.051, Sep. 21, 2015.

Esmaeilzadeh et al., "Production improvement in gas condensate reservoirs by wettability alteration, using superamphiphobic titanium oxide nanofluid", Oil & Gas Science and Technology, vol. 73, No. 46, 2018.

Fahes et al., "Wettability Alteration to Intermediate Gas-Wetting in Gas-Condensate Reservoirs at High Temperature", Society of Petroleum Engineers, SPE Journal, SPE96184, pp. 397-407, Dec. 2007.

Jin et al., "The effect of fluorosurfactant-modified nano-silica on the gas-wetting alteration of sandstone in a CH4-liquid-core system", Fuel, vol. 178, pp. 163-171, 2016.

Li et al., "Experimental Study of Wettability Alteration to Preferential Gas-Wetting in Porous Media and its Effects", SPE Reservoir Eval. & Eng. vol. 3, No. 2, pp. 139-149, Apr. 2000.

Mousavi et al., "Synthesis of fluorinated nano-silica and its application in wettability alternation near-wellbore region In gas condensate reservoirs", Applied Surface Science, vol. 273, pp. 205-214, 2013.

Saboori et al., "Wettability alteration of carbonate rocks from strongly liquid-wetting to strongly gas-wetting by fluorine-doped silica coated by fluorosilane", Journal of Dispersion Science and Technology, vol. 39, No. 6, pp. 767-776, 2018.

Xu et al., "Dopamine as a Robust Anchor to Immobilize Functional Molecules on teh Iron Oxide Shell of Magnetic Nanoparticles", Journal American Chemical Society, vol. 126, pp. 9938-9939, 2004.

European Rule 94(3) Examination Report, dated Mar. 28, 2024, received in corresponding European Application No. 20785648.5, pp. 1-7.

* cited by examiner

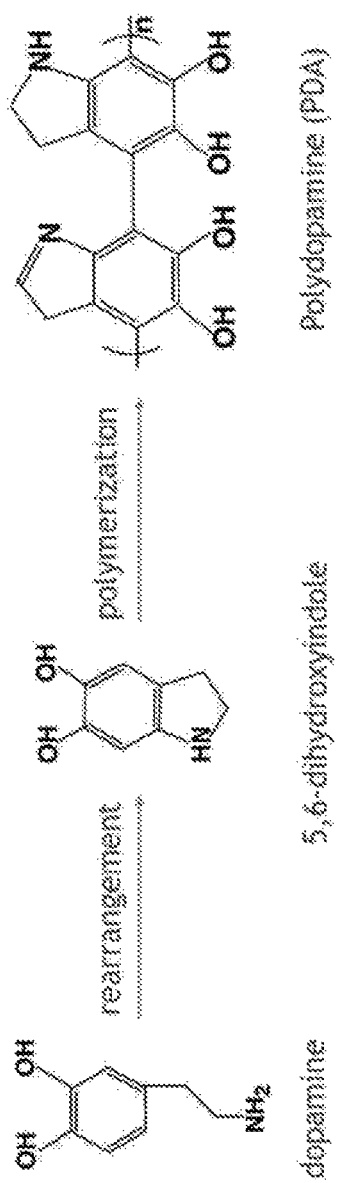

METHODS FOR REDUCING CONDENSATION

CROSS-REFERENCE TO RELATED APPLICATIONS

This application claims the benefit of U.S. Provisional Application Ser. No. 62/908,134 filed Sep. 30, 2019, the entire disclosure of which is hereby incorporated herein by reference.

TECHNICAL FIELD

The present disclosure relates to natural resource well drilling and hydrocarbon production and, more specifically, to methods for reducing condensate.

BACKGROUND

The discovery and extraction of hydrocarbons, such as oil or natural gas, from subsurface formations, may be impeded for a variety of reasons, such as condensate formation in the subsurface formation. Condensate forms in subsurface formations when the downhole pressure is less than the dew point pressure. This may lead to a decreased rate of production of hydrocarbons from a hydrocarbon-producing region of the subsurface formation compared to the expected rate of production. In these instances, methods for reducing condensate in the subsurface formation can be utilized to improve hydrocarbon production. Conventional techniques include gas injection, water-alternating gas, hydraulic fracturing, and side-tracking. The optimal application of each type depends on subsurface formation temperature, pressure, depth, net pay, permeability, residual oil and water saturations, porosity, and hydrocarbon composition. However, these methods are time-consuming and do not result in permanent condensate removal.

SUMMARY

Accordingly, a continuing need exists for efficient methods for reducing condensate in a subsurface formation that result in permanent condensate removal. The present disclosure is directed to compositions and methods for reducing condensate utilizing functionalized silica nanoparticles formed and attached in situ to the subsurface formation. The functionalized silica nanoparticles are hydrophobic, oleophobic, or both, and decrease the surface tension of the subsurface formation, increasing relative permeability and decreasing condensate banking at the wellbore.

In accordance with one or more embodiments of the present disclosure, a method for reducing condensate in a subsurface formation is disclosed. The method includes introducing a reactive mixture including an aqueous solution, urea, dopamine, a silica nanoparticle precursor, a silane grafting compound, and an alcohol compound into the subsurface formation. The method also includes allowing generation of ammonia through thermal decomposition of the urea and allowing the silica nanoparticle precursor to hydrolyze, thereby forming silica nanoparticles. The method further includes allowing the silane grafting compound to graft onto the silica nanoparticles, thereby forming functionalized silica nanoparticles. The method also includes allowing polymerization of the dopamine, thereby forming polydopamine. The method also includes allowing the functionalized silica nanoparticles to attach to the subsurface formation via the polydopamine, thereby reducing condensate in the subsurface formation.

In accordance with one or more embodiments of the present disclosure, a method for increasing a rate of hydrocarbon production from a subsurface formation is disclosed. The method includes producing a first rate of production of hydrocarbons from the subsurface formation through a wellbore. The method also includes introducing a reactive mixture including an aqueous solution, urea, dopamine, a silica nanoparticle precursor, a silane grafting compound, and an alcohol compound into the subsurface formation. The method also includes allowing generation of ammonium hydroxide through thermal decomposition of the urea and allowing the silica nanoparticle precursor to hydrolyze, thereby forming silica nanoparticles. The method further includes allowing the silane grafting compound to graft onto the silica nanoparticles, thereby forming functionalized silica nanoparticles via reactions that occur with a hierarchical order depending on the alkoxy substituent on the silica precursor. The method also includes allowing polymerization of the dopamine, thereby forming polydopamine. The method also includes allowing the functionalized silica nanoparticles to attach to the subsurface formation via the polydopamine, thereby reducing condensate in the subsurface formation. The method further includes increasing hydrocarbon production from the subsurface formation by producing a second rate of production of hydrocarbons from the subsurface formation, in which the second rate of production of hydrocarbons is greater than the first rate of production of hydrocarbons.

Additional features and advantages of the described embodiments will be set forth in the detailed description which follows. The additional features and advantages of the described embodiments will be, in part, readily apparent to those skilled in the art from that description or recognized by practicing the described embodiments, including the detailed description which follows as well as the drawings and the claims.

BRIEF DESCRIPTION OF THE DRAWING

The following detailed description of specific embodiments of the present disclosure may be best understood when read in conjunction with the following drawing, where like structures are indicated with like reference numerals and in which:

FIG. 1 schematically depicts the polymerization mechanism of dopamine, according to one or more embodiments described in this disclosure.

DETAILED DESCRIPTION

As used throughout this disclosure, the term "annulus" refers to the space between two concentric objects, such as between the wellbore and casing, between the wellbore and drillpipe, or between casing and tubing, where fluid can flow.

As used throughout this disclosure, the term "condensate" refers to a liquid hydrocarbon phase that generally occurs in association with natural gas. Its presence as a liquid phase depends on temperature and pressure conditions in the reservoir allowing condensation of liquid from vapor. The API gravity of condensate is typically from 50° to 120°.

As used throughout this disclosure, the term "condensate banking" refers to a relative permeability effect where condensate drops out of the vapor phase around the wellbore when the pressure drops to less than the dew point in response to drawdown or depletion. Gas production rate may be severely reduced by the permeability reduction.

As used throughout this disclosure, the term "hydraulic fracturing" refers to a stimulation treatment routinely performed on hydrocarbon wells in low-permeability reservoirs, such as reservoirs with a permeability of less than 10 milli Darcys (mD). Hydraulic fracturing fluids are pumped into a subsurface formation, causing a fracture to form or open. The wings of the fracture extend away from the wellbore in opposing directions according to the natural stresses within the subsurface formation. Proppant are mixed with the treatment fluid to keep the fracture open when the treatment is complete. Hydraulic fracturing creates communication with a subsurface formation and bypasses damage, such as condensate banking, that may exist in the near-wellbore area.

As used in this disclosure, the term "relative permeability" refers to the measurement of the ability of two or more fluid phases to pass through a subsurface formation. The relative permeability reflects the capability of a specific subsurface formation to produce a combination of oil, water or gas more accurately than the absolute permeability of a formation sample, which is measured with a single-phase fluid, usually water. The term "absolute permeability" refers to the measurement of the permeability, or ability to flow or transmit fluids through a rock, conducted when a single fluid, or phase, is present in the rock. The symbol most commonly used for permeability is k, which is measured in units of Darcies or milliDarcies.

As used in this disclosure, the term "sidetracking" refers to drilling a secondary wellbore away from an original wellbore. Sidetracking may involve bypassing an unusable section of the original wellbore that is no longer efficient to produce from due to various production problems, such as condensate banking. The sidetrack wellbore is conventionally drilled parallel to the original well.

As used throughout this disclosure, the term "subsurface formation" refers to a body of rock that is sufficiently distinctive and continuous from the surrounding rock bodies that the body of rock can be mapped as a distinct entity. A subsurface formation is, therefore, sufficiently homogenous to form a single identifiable unit containing similar properties throughout the subsurface formation, including, but not limited to, porosity and permeability. A subsurface formation is the fundamental unit of lithostratigraphy.

As used throughout this disclosure, the term "packer" refers to a device that can be run into a wellbore with an initial outside diameter smaller than the wellbore which then expands externally to seal the wellbore. The packer isolates the annulus, enabling controlled production, injection, or treatment.

As used throughout this disclosure, the term "producing subsurface formation" refers to the subsurface formation from which hydrocarbons are produced.

As used throughout this disclosure, the term "reservoir" refers to a subsurface formation having sufficient porosity and permeability to store and transmit fluids.

As used throughout this disclosure, the term "water-alternating gas" refers to a condensate removal technique in which water and gas are alternately injected into the subsurface formation.

As used throughout this disclosure, the term "wellbore" refers to the drilled hole or borehole, including the openhole or uncased portion of the well. Borehole may refer to the inside diameter of the wellbore wall, the rock face that bounds the drilled hole.

The present disclosure is directed to methods for reducing condensate in a subsurface formation, in particular to methods for reducing the surface energy of the producing subsurface formation. In hydrocarbon gas production, natural subsurface formation energy displaces hydrocarbons from the subsurface formation into the wellbore and up to the surface. Throughout production, the subsurface formation pressure will decrease and, eventually, condensate will drop out of the hydrocarbon gas. A reduction in the surface energy of the subsurface formation would result in a decrease in the interfacial tension between the subsurface formation and the condensate, increasing the production of the hydrocarbons present in the subsurface formation. The present method includes introducing a reactive mixture comprising an aqueous solution, urea, dopamine, a silica nanoparticle precursor, a silane grafting compound, and an alcohol compound into the subsurface formation. In some embodiments, the method may include introducing the reactive mixture into the producing subsurface formation. The reactive mixture forms functionalized silica nanoparticles downhole that attach to the subsurface formation via polydopamine. These functionalized silica nanoparticles attached to the subsurface formation reduce the surface energy of the subsurface formation and thereby reduce condensate in the subsurface formation.

Introducing the reactive mixture into the subsurface formation may include introducing the reactive mixture in a single aqueous solution. In other embodiments, introducing the reactive mixture includes introducing the aqueous solution, urea, and dopamine into the subsurface formation separately from the silica nanoparticle precursor, the silane grafting compound, and the alcohol compound. In embodiments, introducing the reactive mixture into the subsurface formation may include introducing the reactive mixture into the subsurface formation through coiled tubing. In other embodiments, introducing the reactive mixture into the subsurface formation includes introducing the reactive mixture through an annulus of a wellbore.

In some embodiments, the reactive mixture may be in a single aqueous solution. The aqueous solution may include from 10 to 60 weight percent (wt. %), from 10 to 50 wt. %, from 10 to 40 wt. %, from 10 to 35 wt. %, from 10 to 30 wt. %, from 10 to 25 wt. %, from 10 to 20 wt. %, from 20 to 60 wt. %, from 20 to 50 wt. %, from 20 to 40 wt. %, from 20 to 35 wt. %, from 20 to 30 wt. %, from 20 to 25 wt. %, from 25 to 60 wt. %, from 25 to 50 wt. %, from 25 to 40 wt. %, from 25 to 35 wt. %, from 25 to 30 wt. %, from 30 to 60 wt. %, from 30 to 50 wt. %, from 30 to 40 wt. %, from 30 to 35 wt. %, from 35 to 60 wt. %, from 35 to 50 wt. %, from 35 to 40 wt. %, from 40 to 60 wt. %, from 40 to 50 wt. %, or from 50 to 60 wt. % of the reactive mixture as calculated by a weight of the aqueous solution. Furthermore, the aqueous solution may include one or more of fresh water, salt water, brine, municipal water, formation water, produced water, well water, filtered water, distilled water, sea water, other type of water, or combinations of waters.

As previously discussed, the reactive mixture includes a silica nanoparticle precursor. The silica nanoparticle precursor may be an acrylic aliphatic silica nanoparticle precursor such as a tetraalkyl orthosilicate. In other embodiments, the tetraalkyl orthosilicate silica nanoparticle precursor includes tetramethyl orthosilicate (TMOS), tetraethyl orthosilicate (TEOS), tetrapropyl orthosilicate (TPOS), tetrabutyl orthosilicate (TBOS), or combinations thereof. The silica nanoparticle precursor may include TMOS, TEOS, TPOS, TBOS, glycidoxypropyltrimethoxysilane, aminopropyltriethoxysilane, (methacryloxy)propyltrimethoxysilane, 3 acrylamidopropyltrimethoxysilane, 4 aminobutryltriethoxysilane, aminophenyltrimethoxysilane, carboxyethylsilanetriol sodium, 4 bromobutyltrimethoxysilane, 2 (chloromethyl)allyltrimethoxysilane, hydroxymethyltriethoxysilane, 3 isocyanotopropyltrimethoxysilane, 3 mercaptopropyltrimethoxysilane, allyltrimethoxysilane, or combinations of these.

The method further includes allowing the silica nanoparticle precursor to hydrolyze, thereby forming silica nanoparticles. The silica nanoparticles may form through the Stöber process. The Stöber process is the hydrolysis of an organic silica nanoparticle precursor in an alcoholic solvent, in this case, the hydrolysis of the silica nanoparticle precursor in the alcohol compound. In some embodiments, bases such as ammonium hydroxide and sodium hydroxide may be used as a catalyst. In other embodiments, acids such as acetic acid and hydrogen chloride may be used as a catalyst. The reaction mechanism is shown in Equation 1.

$$Si(OC_nH_{2n+1})_4 + 2H_2O \rightarrow SiO_2 + 4C_nH_{2n+1}OH \quad \text{EQUATION 1}$$

where n is any whole integer. For example, n may be 1 or 2.

Without intending to be bound by theory, as n increases, the rate of the hydrolysis reaction decreases proportionally. For example, the reaction rate for a silica nanoparticle precursor with tetramethyl groups is faster than a silica nanoparticle precursor with tetraethyl groups or a silica nanoparticle precursor with tetrapropyl groups, and so on. Accordingly, in some embodiments, tetramethyl orthosilicate or tetraethyl orthosilicate may be used for relatively rapid silica nanoparticle formation through hydrolysis reaction.

The hydrolysis reaction may occur at a temperature of greater than 30° C., greater than 35° C., greater than 40° C., greater than 45° C., greater than 50° C., greater than 55° C., greater than 60° C., greater than 70° C., or greater than 80° C.

The alcohol compound allows for condensation of the hydrolyzed silane to form silica nanoparticles. The alcohol compound may include $C_1$-$C_8$ alkanols, such as methanol, ethanol, propanol, butanol, pentanol, heptanol, and octyl alcohol. In one embodiment, the alcohol is butanol. The alcohol may include diols such as ethylene glycol and propylene glycol or a triol such as glycerol. Without intending to be bound by theory, butanol may be less flammable than methanol, ethanol, or propanol, meaning that butanol may be safer for oil field applications where the surface temperature may be equal to or greater than 45° C. In embodiments, longer chain alcohols (such as those with a carbon chain greater than or equal to 3, greater than or equal to 4, greater than or equal to 5, greater than or equal to 6, or greater than or equal to 7) may be used, as longer chain alcohols may have a lesser flash point than shorter chain alcohols (such as those with a carbon chain less than or equal to 7, less than or equal to 6, less than or equal to 5, less than or equal to 4, less than or equal to 3, less than or equal to 2, or 1), leading to safer usage in oil field applications where the surface temperature may be equal to or greater than 45° C.

The alcohol compound may have a flash point of from 45° C. to 200° C., from 50° C. to 200° C., from 60° C. to 200° C., from 70° C. to 200° C., from 80° C. to 200° C., from 90° C. to 200° C., from 100° C. to 200° C., from 125° C. to 200° C., from 150° C. to 200° C., from 175° C. to 200° C., from 45° C. to 175° C., from 50° C. to 175° C., from 60° C. to 175° C., from 70° C. to 175° C., from 80° C. to 175° C., from 90° C. to 175° C., from 100° C. to 175° C., from 125° C. to 175° C., from 150° C. to 175° C., from 45° C. to 150° C., from 50° C. to 150° C., from 60° C. to 150° C., from 70° C. to 150° C., from 80° C. to 150° C., from 90° C. to 150° C., from 100° C. to 150° C., from 125° C. to 150° C., from 45° C. to 125° C., from 50° C. to 125° C., from 60° C. to 125° C., from 70° C. to 125° C., from 80° C. to 125° C., from 90° C. to 125° C., from 100° C. to 125° C., from 45° C. to 100° C., from 50° C. to 100° C., from 60° C. to 100° C., from 70° C. to 100° C., from 80° C. to 100° C., from 90° C. to 100° C., from 45° C. to 90° C., from 50° C. to 90° C., from 60° C. to 90° C., from 70° C. to 90° C., from 80° C. to 90° C., from 45° C. to 80° C., from 50° C. to 80° C., from 60° C. to 80° C., from 70° C. to 80° C., from 45° C. to 70° C., from 50° C. to 70° C., from 60° C. to 70° C., from 45° C. to 60° C., from 50° C. to 60° C., or from 45° C. to 50° C. Without intending to be bound by theory, it may be desirable to use an alcohol compound having a flash point greater than the surface temperature in the oil field.

As stated previously, ammonium hydroxide may be used as a catalyst to speed the silica nanoparticle formation. The reactive mixture includes urea. Urea hydrothermally decomposes to release ammonia in the presence of water. The reaction mechanism for the decomposition of urea is shown in Equation 2.

$$CO(NH_2)_2 + 3H_2O \rightarrow 2NH_4^+ + HCO_3^- + OH^- \quad \text{EQUATION 2}$$

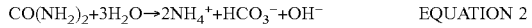

Thus, when the reactive mixture is formed at room temperature and atmospheric pressure, the hydrolysis reaction to form the silica nanoparticles is slow due to the lack of catalyst because the ammonium hydroxide catalyst only forms after the urea decomposes at a temperature of greater than or equal to 70° C., greater than or equal to 75° C., greater than or equal to 80° C., greater than or equal to 85° C., greater than or equal to 90° C., or greater than or equal to 100° C. Therefore, the method further includes allowing in situ generation of ammonia through thermal decomposition of the urea. When the reactive mixture is introduced into the subsurface formation, the temperature of the subsurface formation causes the urea to decompose and form the ammonia catalyst, thereby speeding the hydrolysis reaction and the formation of the silica nanoparticles.

The reactive mixture further includes a silane grafting compound. The silane grafting compound may include a halosilane. A halosilane is any halogen-substituted silane with at least one of alkyl-containing, fluoroalkyl-containing, perfluoroalkyl-containing, organosilane-containing, or aromatic-containing groups. The silane grafting compound may comprise fluorine, chlorine, bromine, iodine, or combinations of these attached to a silane group. One nonlimiting example of a halosilane with a fluoroalkyl group is 1H,1H, 2H,2H-perfluoroalkyltriethoxysilane. In some embodiments, the silane grafting compound includes perfluoroalkyltriethoxysilane, such as perfluorooctyltriethoxysilane, perfluorooctyltrichlorosilane, nanofluorohexyltrichlorosilane, tridecafluoro-1,1,2,2-tetrahydrooctyltrichlorosilane, heptadecafluoro-1,1,2,2-tetrahydrodecyltrichlorosilane, 1H,1H,2H,2H-perfluorodecyltriethoxysilane, perfluorodecyltrichlorosilane, or combinations of these.

As stated previously, tetramethyl orthosilicate (TMOS) or tetraethyl orthosilicate (TEOS) may be used for relatively rapid silica nanoparticle formation through fast hydrolysis reaction. In conjunction with this reaction, fluorinated functional groups are grafted on the silica nanoparticles through a slower reaction with the silane grafting compound. Therefore, the method further includes allowing the silane grafting compound to graft onto the silica nanoparticles, thereby forming functionalized silica nanoparticles via the hierarchical reaction order. In some embodiments, the grafting yields a functionalized layer on the surface of the silica nanoparticles. The reaction mechanism for the decomposition of urea is shown in Equation 3.

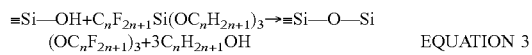

EQUATION 3

This forms functionalized silica nanoparticles having a surface that is hydrophobic, oleophobic, or both. The surface of the functionalized silica nanoparticles may have a surface energy of less than 50 milli Joules per square meter (mJ/m$^2$), less than 40 mJ/m$^2$, less than 38 mJ/m$^2$, less than 37 mJ/m$^2$, less than 36 mJ/m$^2$, less than 35 mJ/m$^2$, less than 33 mJ/m$^2$, less than 31 mJ/m$^2$, less than 30 mJ/m$^2$, less than 29 mJ/m$^2$, less than 25 mJ/m$^2$, less than 20 mJ/m$^2$, less than 18 mJ/m$^2$, less than 15 mJ/m$^2$, less than 10 mJ/m$^2$, or less than 5 mJ/m$^2$.

The method further includes allowing polymerization of the dopamine, thereby forming polydopamine. The dopamine may polymerize in water at temperatures greater than or equal to 70° C., greater than or equal to 75° C., greater than or equal to 80° C., greater than or equal to 85° C., greater than or equal to 90° C., or greater than or equal to 100° C. to form polydopamine. FIG. 1 shows the polymerization of dopamine to polydopamine. Specifically, dopamine rearranges to form a ring at temperatures greater than 100° C., or at least above 70° C. The ringed dopamine then polymerizes to form polydopamine. Upon or after the formation of the silica nanoparticles or functionalized silica nanoparticles, the polydopamine will adhere to the surfaces of both the functionalized silica nanoparticles and the subsurface formation, thereby attaching the functionalized silica nanoparticles to the subsurface formation. Additional information on polydopamine adherence may be found in the article entitled "The Chemistry Behind Catechol-Based Adhesion" by Saiz-Poseu et al., in Angewante International Edition 2019, 58, 696 and the article entitled "Single-Molecule Mechanics of Mussel Adhesion" by Lee et al, in Proceedings of the National Academy of Sciences in the United States of America (PNAS), 2006, 103, 12999, the disclosures of which are incorporated herein by reference in their entirety.

The method may further include introducing a buffer solution with the reactive mixture into the subsurface formation. Use of a buffer solution delays the reaction until the reactive mixture is within the subsurface formation. The buffer solution may include at least one of citric acid, acetic acid, monopotassium phosphate, N-cyclohexyl-2-aminoethanesulfonic acid, and borate. The buffer solution may be soluble in water, may have a very low absorbance of from 240 nanometers (nm) to 700 nm, and may have a pKa value of from 6.0 and 8.0, where the pKa value represents the acid dissociation constant at logarithmic scale.

Without intending to be bound by theory, allowing the functionalized silica nanoparticles to attach to the subsurface formation may thereby increase a water contact angle, an oil contact angle, or both on the subsurface formation from less than 90° to greater than or equal to 90°. In other embodiments, the water contact angle, the oil contact angle, or both may increase from less than 105° to greater than or equal to 105°, from less than 100° to greater than or equal to 100°, from less than 95° to greater than or equal to 95°, from less than 80° to greater than or equal to 80°, from less than 75° to greater than or equal to 75°, from less than 70° to greater than or equal to 70°, from less than 65° to greater than or equal to 65°, from less than 60° to greater than or equal to 60°, from less than 55° to greater than or equal to 55°, from less than 50° to greater than or equal to 50°, or from less than 45° to greater than or equal to 45°.

Without intending to be bound by theory, the reactive mixture may be stable at room temperature and atmospheric pressure, but may be reactive at temperatures greater than 40° C. and pressures greater than 14.7 pounds per square feet (psi). Accordingly, the reactive mixture may be chemically stable at the surface of the wellsite for approximately 12 hours, but may be reactive downhole. The subsurface formation may have a temperature of greater than or equal to 100° C. In other embodiments, the subsurface formation may have a temperature of greater than or equal to 50° C., greater than or equal to 60° C., greater than or equal to 70° C., greater than or equal to 80° C., greater than or equal to 90° C., greater than or equal to 110° C., greater than or equal to 120° C., greater than or equal to 130° C., greater than or equal to 140° C., greater than or equal to 150° C., or greater than or equal to 200° C.

Among other benefits, the methods disclosed increase the permeability of the subsurface formation by reducing the surface tension of the subsurface formation, thereby reducing the interfacial tension between the subsurface formation and the condensate. In turn, this reduces condensate banking. Furthermore, when the functionalized silica nanoparticles attach to the subsurface formation, the nanoparticles create hierarchical roughness on the subsurface formation, which reduces the likelihood of condensate banking forming. Gas injection, water-alternating gas, hydraulic fracturing, and side-tracking are conventional methods used to decrease condensate banking. However, although hydraulic fracturing increases the permeability of the subsurface formation near the wellbore, it does not remove the condensate. Similarly, gas injection, sidetracking, and water-alternating gas each remove the condensate temporarily. However, these techniques do not remove the condensate permanently, as they do not create hierarchical roughness on the subsurface formation and the surface energy and interfacial tension of the subsurface formation remains unchanged. Other benefits may be realized by the methods and compositions described in this disclosure.

The methods disclosed may increase the relative permeability of the subsurface formation by at least 20 mD, at least 50 mD, at least 75 mD, at least 90 mD, at least 100 mD, at least 110 mD, at least 120 mD, at least 150 mD, at least 200 mD, at least 300 mD, or at least 500 mD.

In some embodiments, the reactive mixture may be introduced into the subsurface formation using coiled tubing or a drill string. In embodiments where the aqueous solution, urea, and dopamine are introduced into the subsurface formation separately from the silica nanoparticle precursor, the silane grafting compound, and the alcohol compound, the aqueous solution, urea, and dopamine may be introduced into the subsurface formation using coiled tubing or a drill string and the silica nanoparticle precursor, the silane grafting compound, and the alcohol compound may be introduced into the subsurface formation through the annulus. In embodiments where the aqueous solution, urea, and dopamine are introduced into the subsurface formation separately from the silica nanoparticle precursor, the silane grafting compound, and the alcohol compound, the silica nanoparticle precursor, the silane grafting compound, and the alcohol compound may be introduced into the subsurface formation using coiled tubing or a drill string and the aqueous solution, urea, and dopamine may be introduced into the subsurface formation through the annulus. This configuration allows the reactive mixture to form at a specified depth and be squeezed into the subsurface formation simultaneously. This configuration avoids reaction prior to entering the subsurface formation. In some embodiments, packers may be used to ensure that the reactive mixture enters the subsurface formation at a specified depth.

A method for increasing hydrocarbon production from a subsurface formation is also disclosed. The method includes producing a first rate of production of hydrocarbons from the subsurface formation through a wellbore and introducing a reactive mixture comprising an aqueous solution, urea, dopamine, a silica nanoparticle precursor, a silane grafting compound, and an alcohol compound into the subsurface formation. The subsurface formation may be a producing subsurface formation. The method further includes allowing generation of ammonia through thermal decomposition of the urea and allowing the silica nanoparticle precursor to hydrolyze, thereby forming silica nanoparticles. The method further includes allowing the silane grafting compound to graft onto the silica nanoparticles, thereby forming functionalized silica nanoparticles and allowing polymerization of the dopamine, thereby forming polydopamine. The method further includes allowing the functionalized silica nanoparticles to attach to the subsurface formation via the polydopamine, in which the functionalized silica nanoparticles reduce a first interfacial tension between the hydrocarbons and the subsurface formation to a second interfacial tension, thereby reducing condensate in the subsurface formation. Then, after introducing the reactive mixture, the method further includes increasing hydrocarbon production from the subsurface formation by producing a second rate of production of hydrocarbons from the subsurface formation. The second rate of production of hydrocarbons may be greater than the first rate of production of hydrocarbons.

EXAMPLE

The following example illustrates features of the present disclosure but is not intended to limit the scope of the disclosure.

To demonstrate the reduced surface energy of subsurface formations treated with the reactive mixture of this disclosure, rock samples were treated with a reactive mixture as described in this disclosure. To form the reactive mixture, (1) 0.25 mL of an aqueous solution including 97% 1H,1H,2H,2H-perfluoroalkyltriethoxysilane (available from Alfa Aesar, headquartered in Ward Hill, Massachusetts) and 1.0 mL of an aqueous solution including greater than or equal to 98% tetramethyl orthosilicate (available from Honeywell Fluka™, headquartered in New Jersey) were mixed in 2.0 mL of butanol (Certified ACS, available from Fisher, headquartered in Hampton, New Hampshire); and (2) 0.05 g of an aqueous solution including 99% dopamine hydrochloride (available from Alfa Aesar) and 0.2 g urea (Certified ACS, available from Fisher, headquartered in Hampton, New Hampshire) were dissolved in 2.0 mL water. These two mixtures were then combined to form the reactive mixture. The reactive mixture is stable at room temperature and pressure for approximately 12 hours. The reactive mixture was then mixed with 5.0 g quartz rock grains in an autoclave at a temperature of 100° C. for 12 hours. This experiment was repeated for sandstone and limestone rock grains. The rock samples were then rinsed with an aqueous cleaning solution including ethanol (190 proof, 95% ethanol, Reagent ACS, available from Fisher, headquartered in Hampton, New Hampshire).

After this treatment, the surface energy of the sandstone reduced such that the surface changed from hydrophilic to hydrophobic. Specifically, after treatment, the sandstone had a water contact angle of 107° and a crude oil contact angle of 67°. Additionally, after treatment, the limestone had a water contact angle of 90° and a crude oil contact angle of 77°. Furthermore, when a droplet of crude oil was placed on the rock sample surface, the spreading and immersion of the oil droplet in the rock sample was slowed as compared to a droplet of crude oil on an untreated rock sample surface. This indicates some oleophobicity on the surface of the rock sample as well as hydrophobicity.

It is noted that one or more of the following claims utilize the term "where" or "in which" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B, and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

It should be understood that any two quantitative values assigned to a property may constitute a range of that property, and all combinations of ranges formed from all stated quantitative values of a given property are contemplated in this disclosure. The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

What is claimed is:

1. A method for reducing condensate in a subsurface formation, the method comprising:
   introducing a reactive mixture comprising an aqueous solution, urea, dopamine, a silica nanoparticle precursor, a silane grafting compound, and an alcohol compound into the subsurface formation;
   generating ammonia through thermal decomposition of the urea;
   hydrolyzing the silica nanoparticle precursor, thereby forming silica nanoparticles;
   grafting the silane grafting compound onto the silica nanoparticles, thereby forming functionalized silica nanoparticles;
   polymerizing the dopamine, thereby forming polydopamine; and
   attaching the functionalized silica nanoparticles to the subsurface formation via the polydopamine, thereby reducing condensate in the subsurface formation.

2. The method of claim 1, in which the reactive mixture is in a single aqueous solution.

3. The method of claim 1, in which introducing the reactive mixture comprises introducing the aqueous solution, urea, and dopamine into the subsurface formation separately from the silica nanoparticle precursor, the silane grafting compound, and the alcohol compound.

4. The method of claim 1, further comprising introducing a buffer solution with the reactive mixture into the subsurface formation.

5. The method of claim 1, in which attaching the functionalized silica nanoparticles to the subsurface formation thereby increases a water contact angle, an oil contact angle, or both on the subsurface formation from less than 90° to greater than or equal to 90°.

6. The method of claim 1, in which the subsurface formation has a temperature of greater than or equal to 70° C.

7. The method of claim 1, in which the silica nanoparticle precursor comprises a tetraalkyl orthosilicate.

8. The method of claim 1, in which the silica nanoparticle precursor comprises tetramethyl orthosilicate, tetraethyl orthosilicate, tetrapropyl orthosilicate, tetrabutyl orthosilicate, glycidoxypropyltrimethoxysilane, aminopropyltriethoxysilane, (methacryloxy) propyltrimethoxysilane, 3 acrylamidopropyltrimethoxysilane, 4 aminobutryltriethoxysilane, aminophenyltrimethoxysilane, carboxyethylsilanetriol sodium, 4 bromobutyltrimethoxysilane, 2 (chloromethyl) allyltrimethoxysilane, hydroxymethyltriethoxysilane, 3 isocyanotopropyltrimethoxysilane, 3 mercaptopropyltrimethoxysilane, or allyltrimethoxysilane, or combinations of these.

9. The method of claim 1, in which the silane grafting compound comprises fluorine, chlorine, bromine, iodine, or combinations of these attached to a silane group.

10. The method of claim 1, in which the silane grafting compound comprises perfluorooctyltriethoxysilane, perfluorooctyltrichlorosilane, nanofluorohexyltrichlorosilane, tridecafluoro-1,1,2,2-tetrahydrooctyltrichlorosilane, heptadecafluoro-1,1,2,2-tetrahydrodecyltrichlorosilane, 1H,1H,2H,2H-perfluorodecyltriethoxysilane, perfluorodecyltrichlorosilane, or combinations of these.

11. The method of claim 1, in which the alcohol compound comprises butanol.

12. A method for increasing a rate of hydrocarbon production from a subsurface formation, the method comprising:
   producing a first rate of production of hydrocarbons from the subsurface formation through a wellbore;
   introducing a reactive mixture comprising an aqueous solution, urea, dopamine, a silica nanoparticle precursor, a silane grafting compound, and an alcohol compound into the subsurface formation;
   generating ammonia through thermal decomposition of the urea;
   hydrolyzing the silica nanoparticle precursor, thereby forming silica nanoparticles;
   grafting the silane grafting compound onto the silica nanoparticles, thereby forming functionalized silica nanoparticles;
   polymerizing the dopamine, thereby forming polydopamine;
   attaching the functionalized silica nanoparticles to the subsurface formation via the polydopamine, in which the functionalized silica nanoparticles reduce a first interfacial tension between the hydrocarbons and the subsurface formation to a second interfacial tension, thereby reducing condensate in the subsurface formation; and
   increasing hydrocarbon production from the subsurface formation by producing a second rate of production of hydrocarbons from the subsurface formation, in which the second rate of production of hydrocarbons is greater than the first rate of production of hydrocarbons.

13. The method of claim 12, in which the reactive mixture is in a single aqueous solution.

14. The method of claim 12, in which introducing the reactive mixture comprises introducing the aqueous solution, urea, and dopamine into the subsurface formation separately from the silica nanoparticle precursor, the silane grafting compound, and the alcohol compound.

15. The method of claim 12, in which attaching the functionalized silica nanoparticles to the subsurface formation thereby increases a water contact angle, an oil contact angle, or both on the subsurface formation from less than 90° to greater than or equal to 90°.

16. The method of claim 12, in which the subsurface formation has a temperature of greater than or equal to 70° C.

17. The method of claim 12, in which the silica nanoparticle precursor comprises tetramethyl orthosilicate, tetraethyl orthosilicate, tetrapropyl orthosilicate, tetrabutyl orthosilicate, glycidoxypropyltrimethoxysilane, aminopropyltriethoxysilane, (methacryloxy) propyltrimethoxysilane, 3 acrylamidopropyltrimethoxysilane, 4 aminobutryltriethoxysilane, aminophenyltrimethoxysilane, carboxyethylsilanetriol sodium, 4 bromobutyltrimethoxysilane, 2 (chloromethyl) allyltrimethoxysilane, hydroxymethyltriethoxysilane, 3 isocyanotopropyltrimethoxysilane, 3 mercaptopropyltrimethoxysilane, or allyltrimethoxysilane, or combinations of these.

18. The method of claim 12, in which the silane grafting compound comprises fluorine, chlorine, bromine, iodine, or combinations of these attached to a silane group.

19. The method of claim 12, in which the silane grafting compound comprises perfluoroalkyltriethoxysilane, perfluorooctyltriethoxysilane, perfluorooctyltrichlorosilane, nanofluorohexyltrichlorosilane, tridecafluoro-1,1,2,2-tetrahydrooctyltrichlorosilane, heptadecafluoro-1,1,2,2-tetrahydrodecyltrichlorosilane, 1H,1H,2H,2H- perfluorodecyltriethoxysilane, perfluorodecyltrichlorosilane, or combinations of these.

20. The method of claim 12, in which the alcohol compound comprises butanol.

* * * * *